United States Patent [19]

Rogers et al.

[11] 4,429,049
[45] Jan. 31, 1984

[54] METHOD FOR THE ANALYSIS OF ORGANIC POLLUTANTS

[75] Inventors: Calvin Rogers; Russell A. Parker, both of Durham, N.C.; Terry L. Loucks, Red Bank, N.J.

[73] Assignee: Mead Corporation, Dayton, Ohio

[21] Appl. No.: 350,689

[22] Filed: Feb. 22, 1982

[51] Int. Cl.³ .................... G01N 1/00; B01D 11/04
[52] U.S. Cl. ................................ 436/178; 422/101; 422/257; 436/104
[58] Field of Search .............. 239/548, 561; 422/68, 422/101, 256, 257; 436/174, 178, 104

[56] References Cited

U.S. PATENT DOCUMENTS

| | | | |
|---|---|---|---|
| 2,249,746 | 7/1941 | Colbeth | 422/256 |
| 2,466,182 | 4/1949 | Peeps | 239/548 X |
| 2,689,874 | 9/1954 | Findlay | 422/256 X |
| 2,729,549 | 1/1956 | Reman et al. | 422/256 X |
| 3,204,934 | 9/1965 | Graham et al. | 422/256 X |
| 3,212,854 | 10/1965 | Betts et al. | 422/256 X |
| 3,226,092 | 12/1965 | Graham et al. | 422/256 X |
| 3,247,104 | 4/1966 | Sako et al. | 422/256 X |
| 3,260,572 | 7/1966 | Faugeras et al. | 422/256 X |
| 3,403,980 | 10/1968 | Litterio | 422/256 X |
| 3,966,410 | 6/1976 | Jahnsen | 436/178 |
| 4,258,010 | 3/1981 | Rozsa et al. | 422/257 |
| 4,267,056 | 5/1981 | McClure | 436/178 X |

Primary Examiner—Arnold Turk
Attorney, Agent, or Firm—Biebel, French & Nauman

[57] ABSTRACT

A process for the analysis of organic pollutants from an aqueous sample is provided including injecting an extraction solvent under pressure in the form of a plurality of substantially uniform droplets into the sample containing one or more pollutants. The solvent droplets are collected and then analyzed for the presence of the pollutants. The apparatus includes a sample holding column, a solvent reservoir, a source of gas under pressure, and a nozzle having one or more outlet ports which subdivides the solvent into small uniform droplets to enhance mass transfer of pollutants from the sample into the solvent.

17 Claims, 4 Drawing Figures

METHOD FOR THE ANALYSIS OF ORGANIC POLLUTANTS

BACKGROUND OF THE INVENTION

The present invention relates to an analytical apparatus and process, and more particularly to an apparatus and process for extracting pollutants from a waste water sample under pressure as a necessary step to analyzing the concentrations of such pollutants in the waste water sample.

Liquid-liquid contacting systems for use in solvent extraction operations are widely used. A principal object in the use of such systems is the contacting of immiscible or only partially miscible liquids to cause the transfer of dissolved substances from one liquid to another. Some such examples of prior art extraction systems are disclosed in U.S. Pat. Nos. 2,249,746; 3,260,572; 2,729,549; 3,403,980; 2,689,874; 3,226,092; 3,212,854 and 3,247,104.

In the area of monitoring and sampling water and waste water streams for pollutants, solvent extraction techniques have found use in extracting organic chemical compounds from the aqueous streams. The U.S. Environmental Protection Agency has issued regulations pursuant to section 304(h) of the Clean Water Act, 33 U.S.D. 1251 et. seq., which requires the agency to promulgate guidelines establishing test procedures for the analysis of pollutants. See generally 40 C.F.R. 136.

Although the ultimate analysis of many organic pollutants is performed using gas or liquid chromatography and mass spectrometry techniques, in many instances the organic pollutants are initially extracted from the water samples using solvent extraction. This is true for the analysis of pesticides and polynuclear aromatic hydrocarbon compounds as well as base/neutral and acid compounds.

At present, the two USEPA approved extraction methods are solvent extractions with vigorous manual shaking in a separatory funnel and a extraction technique in which a solvent having a higher specific gravity than water is passed through a continuous column of water containing the pollutant to be extracted and repeatedly recycled for an extended time period. However, each technique has significant disadvantages. The manual technique sometimes results in emulsions which are difficult and/or time consuming to break, requires the time and attention of a trained technician, and yields variable recoveries of extracted compounds. The continuous extraction technique, while being less subject to the formation of emulsions and requiring only relatively unattended operation, requires 24 to 48 hours to achieve one extraction, requires apparatus which is difficult to clean because of its complicated design and subject to breakage, and requires significant amounts of electrical power and cooling water to operate.

Accordingly, there exists a need in the art for an extracting and analyzing procedure which is relatively rapid, simple to use, and avoids the problems of prior art techniques.

SUMMARY OF THE INVENTION

The present invention meets that need by providing a procedure whereby organic pollutants are first extracted from waste streams such as water and waste water streams and thereafter analyzed. In accordance with one aspect of the present invention, a sample containing one or more organic pollutants is placed in a column and an extraction solvent is injected under pressure into this chamber to produce a plurality of substantially uniform droplets. As these droplets of extraction solvent pass through the sample, pollutants diffuse through the interface between the solvent and sample. The droplets of the solvent which now contains the extracted pollutants are then collected as an extract solution and the solution is analyzed to determine the presence and/or concentration of one or more of the pollutants.

The apparatus for carrying out the practice of the present invention includes a source of inert gas under pressure, a reservoir containing a suitable extraction solvent, a column for holding the sample, and a solvent injector. The gas under pressure forces the solvent in the form of substantially uniform droplets through the solvent injector into the sample column. In a preferred embodiment of the invention, the injector is a long needle-like nozzle element having an outlet port at its tip and at least one other opening on the side of the element. The openings are sized to expel droplets of solvent having relatively small mean drop diameters. The inert gas pressure is regulated to generate individual droplets of appropriate size.

In a preferred embodiment of the invention, the solvent selected to extract the pollutants in the aqueous sample has a higher specific gravity than the sample. As droplets are injected under pressure into the sample, they fall through it and collect at the bottom of the sample holding column. During the period that these droplets are falling through the sample, extractable pollutants in the sample diffuse into the droplets. Contacting of the two liquid phases and mass transfer of pollutants between them may be enhanced through the use of an agitator in the sample holding column. The pollutant containing extract solution is then removed from the sample column and analyzed.

In certain instances, the sample to be treated may contain both organic pollutants which are more readily extracted from media having a basic pH and pollutants which are more readily extracted from media having an acidic pH. In those instances, it is desirable to adjust the pH of the sample to a basic pH, perform an initial extraction of base/neutral pollutants, and collect the pollutant containing extract solution. Then, the pH of the sample is adjusted to an acidic pH, the acid pollutants extracted, and a second pollutant containing extract solution is collected. The two extract solution portions can then be analyzed separately or combined and a single pollutant analysis performed. In other instances, the extraction may take place at a neutral pH.

Accordingly, it is an object of the present invention to provide a relatively rapid and reliable extraction process and apparatus which is simple and inexpensive to use. This and other objects and advantages of the invention will become apparent from the following description, the accompanying drawings, and the appended claims.

DESCRIPTION OF THE PREFERRED EMBODIMENTS

Figure 1:
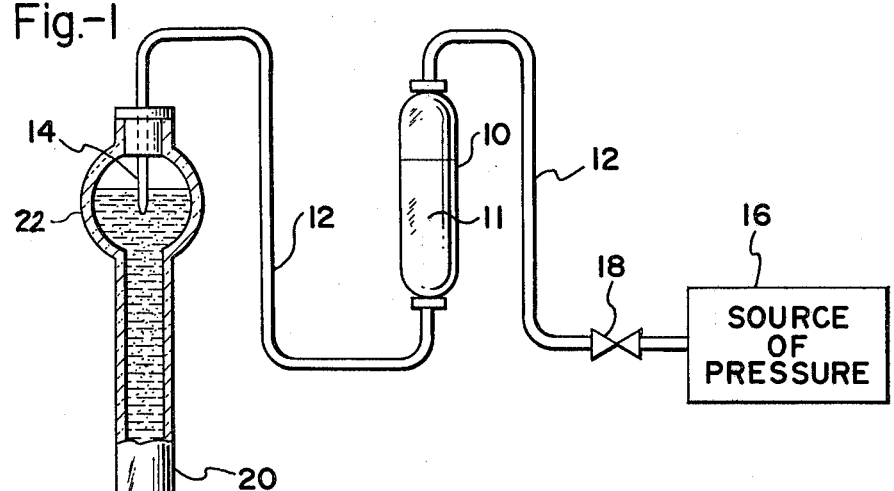
FIG. 1 is a schematic diagram of the extraction process and apparatus of the present invention.

Referring now to FIG. 1, a schematic diagram of the present invention is illustrated in which solvent 11 from solvent reservoir 10 is forced through line 12 into nozzle 14 by gas pressure from gas pressure source 16. The pressure maintained in line 12 is regulated by control valve 18. Preferably, an inert gas such as nitrogen is used as the pressuring gas. The pressure, in conjunction with the nozzle outlet port diameters, effectively controls the mean droplet size of solvent droplets produced.

As shown, sample holding column 20 may be an elongated glass tube having a larger diameter bulb 22 located near the upper end thereof and an outlet valve 24 located at the lower end thereof. The volume of liquid that column 20 can hold may vary and is dependent upon the size of the sample. Generally, the holding column 20 should be able to hold sample sizes in the range of between 1 and 20 liters, preferably about 1 liter plus the additional volume of solvent required for extraction. Use of an elongated holding column is preferred, since this will increase both the contact and the contact time of solvent droplets with the aqueous sample and result in an increase recovery efficiency of pollutants being diffused into the solvent droplets from the aqueous sample. The design of the chamber should also be such that the outlet ports on injection nozzle 14 will always be submerged beneath the initial sample level in the column.

In a preferred embodiment, the solvent chosen to extract pollutants from the aqueous sample will have a specific gravity greater than 1. In this manner, the substantially uniform droplets of solvent formed at nozzle 14 will fall through the aqueous sample in a single pass and collect at the bottom of sample holding column 20 where the extract solution can then be drawn off through outlet valve 24. The choice of solvent will of course depend on several factors including its specific gravity, immiscibility with water, and preferential solubility with the particular pollutant or pollutants to be extracted. For most base/neutral, acid, and pesticide extractable compounds, the preferred solvent is methylene chloride. However, other suitable solvents such as chloroform may also be utilized. If it is desired to use a solvent with a specific gravity of less than 1, hexane and ethyl ether may be used. In such a situation the solvent droplet would rise rather than settle in the column 20.

Figure 2:
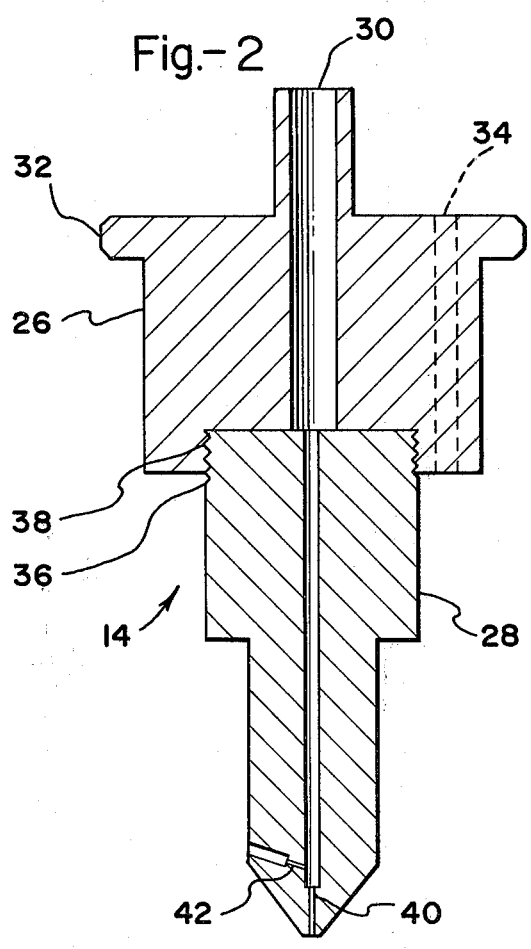
FIG. 2 is an enlarged sectional view of an injector nozzle which may be used in the practice of the present invention.

As best shown in FIG. 2, the injector nozzle 14 of the present invention has an upper cap portion 26 and a lower needle-like portion 28. Cap portion 26 has an inlet 30 which is connected to line 12 to provide a source of solvent to the nozzle. Flange or lip 32 fits over the opening in the top of chamber 20 to provide a seal between the chamber and nozzle. Air escape hole 34 is provided to relieve air pressure inside chamber 20 as solvent displaces the air which is initially present in the column.

Needle-like portion 28 is provided with threads 36 which mate with corresponding threads 38 on cap portion 26 to join the two portions. A first outlet port 40 is provided at the end of portion 28 through which discrete droplets of solvent pass. A second outlet port 42 is provided on the side of portion 28 which facilitates the mingling of solvent droplets with the aqueous sample as the aqueous sample level rises due to solvent build-up. As shown, outlet port 42 is angled upwardly from horizontal at between about 5° to 25°, preferably 18° which has been found to improve the mingling of solvent droplets with the aqueous sample. Of course, additional outlet ports may be added, if desired.

Preferably, nozzle 14 is fabricated of a material which is unaffected by both the solvent and aqueous samples. Such materials may include metals, such as brass and stainless steel or synthetic material, such as Teflon.

It is to be understood that the choice of the particular size of the outlet port diameter and the choice of the pressure applied to the solvent will determine the resulting mean diameter of the droplets exiting from the outlet ports. For the efficient operation of the process, the particular choice of the variable should be such that the mean diameter of the droplets be small enough in order to provide sufficient surface area for an efficient mass transfer reaction to take place between the solvent and a substantial amount of the pollutants in the aqueous sample and yet not be too small to retard the movement of the droplets from one end of the column to the other thereby unduly delaying the completion of the extraction step prior to performing the analysis of the extract solution.

With the use of methylene chloride, for example, as the solvent, it has been found that a minimum of at least about 6 seconds of contact time is required for efficient mass transfer to take place. Therefore, utilizing a column which carries a length in the range of from about 15 to 45 inches, the pressure applied to the solvent should be in the range of about 20 to 40 psi, preferably 25 to 30 psi, with the diameter of the outlet port being about 0.004 inches to 0.008 inches, preferably 0.005 inches to 0.007 inches. The resulting droplet mean diameter size would be about 0.004 inches to 0.08 inches, preferably 0.01 inches to 0.02 inches.

Figure 4:
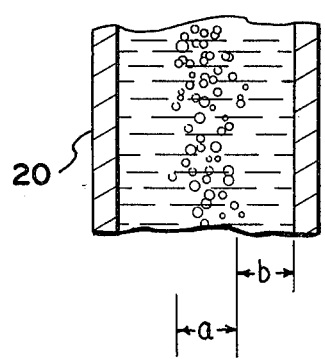
FIG. 4 is an enlarged sectional view of a portion of the column shown in FIG. 1.

Further, in order to provide sufficient contact between the solvent droplets and substantially all of the pollutant contained within the aqueous sample, the particular cross sectional dimension of the column should not be so large as to provide an area of aqueous sample that would be beyond the contact reach of the descending droplets as they move through the column from one end to the other. FIG. 4 illustrates this undesirable occurrence with the reference a defining the area of the descending droplets within the column where intermixing of the droplets with the aqueous sample occurs and with the reference b defining that area where there is no intermixing of the droplets with the aqueous sample. It has been fond that the diameter of the column should not exceed about 5 inches, and should preferably be between 1.5 and 2.5 inches.

To eliminate the possibility of that portion of the aqueous sample (located at or above the level of the outlet port 40 of the nozzle 14) not coming into contact with the droplets that would be ejected from the outlet port 40 projecting along the length of the column, one or more additional outlet ports 42 could be arranged to project droplets of solvent up into the area above the tip of the outlet port 40. This arrangement effectively enhances the ability of the droplet to come into intimate contact with substantially all of the aqueous sample and, thus, provide for an efficient single pass extraction step.

The amount of the aqueous sample that is introduced in the column 20 is generally governed by the test protocol or guideline. Generally, about 1 liter samples are used. The amount of solvent that would correspondingly be used is selected in proportion to the amount of the aqueous sample that is carried in the column 20. It is important that there be sufficient solvent utilized in the single pass extraction such that substantially all of the selected pollutants are extracted into the solvent for subsequent analysis. Therefore, in the case where selected base/neutral compounds or acid compounds are to be selectively extracted, it has been found that from about 50 to about 300 ml, preferably 180 ml, of solvent may be used in order to provide sufficient solvent to extract out substantially all of such selected compounds.

Figure 3:
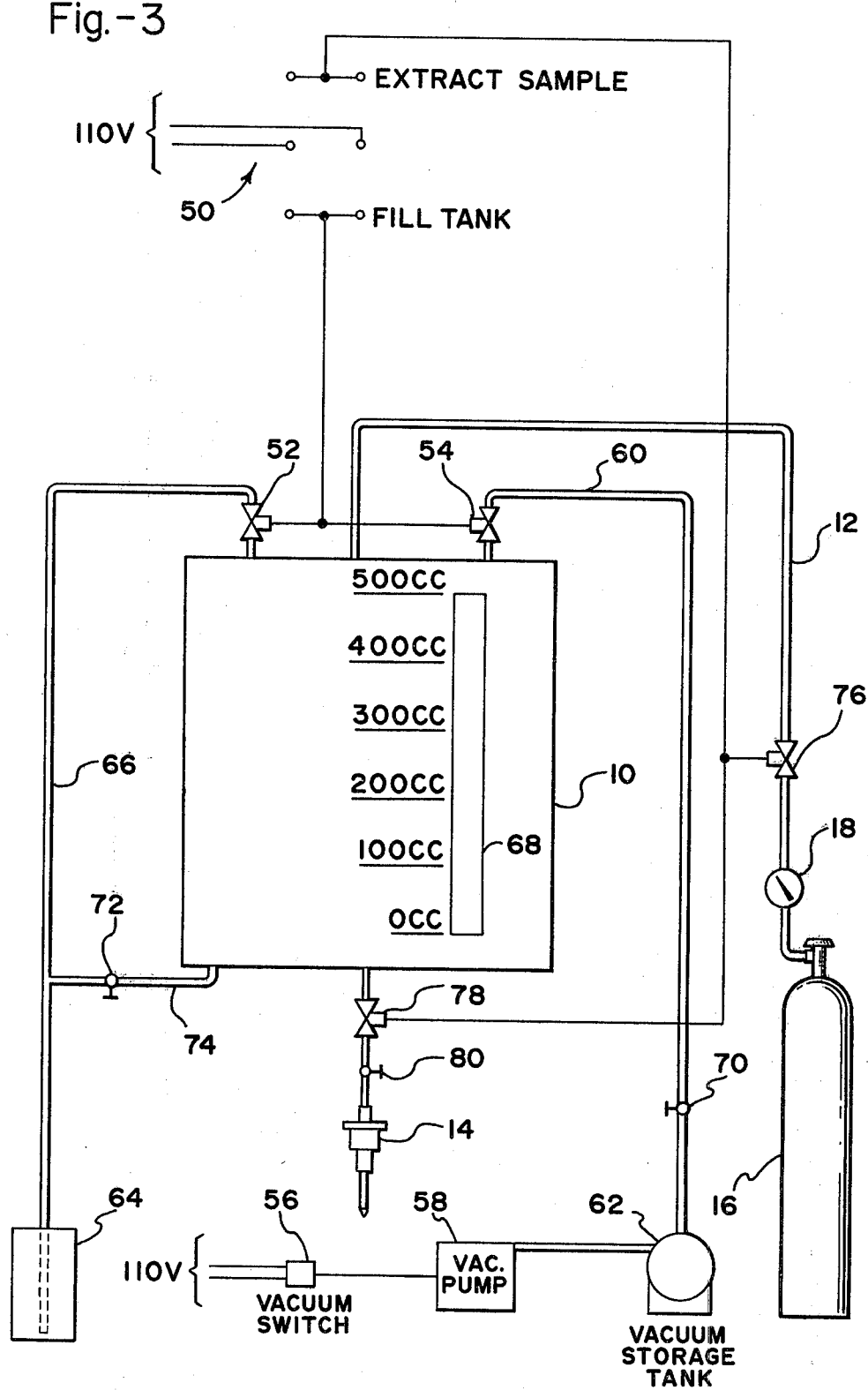
FIG. 3 is a schematic diagram of an automated embodiment of the present invention.

An automated version of the present invention is illustrated schematically in FIG. 3, where like numerals represent like elements. The system is activated by throwing three pole toggle switch 50 into the "FILL TANK" position which activates and opens normally closed solenoid valves 52 and 54. At the same time, vacuum switch 56 is turned on, activating vacuum pump 58. The action of vacuum pump 58 through line 60 and vacuum storage tank 62 lowers the pressure inside solvent reservoir 10. This in turn causes solvent to be drawn from holding tank 64 through line 66 into reservoir 10. When a predetermined amount of solvent has filled reservoir 10 as determined, for example, by observation through view port 68 having volume markings adjacent thereto, switches 56 and 50 are deactivated causing valves 52 and 54 to close. Throttling valve 70 in line 60 can be adjusted to control the vacuum being pulled on reservoir 10 while needle valve 72 in line 74 can be used to make minor adjustments to the level of solvent maintained in reservoir 10.

Extraction of the sample is commenced by throwing toggle switch 50 to the "EXTRACT SAMPLE" position which activates normally closed solenoid valves 76 and 78 causing them to open. This causes gas from gas pressure source 16 to increase the pressure in reservoir 10 and solvent to flow into nozzle 14. Flow control valve 80 may be adjusted to provide the desired rate of flow of solvent into nozzle 14.

The process and apparatus of the present invention can be used to extract a wide variety of organic pollutants from water and waste water samples. Such pollutants include organo-chlorine pesticides, polynuclear aromatic hydrocarbons, base/neutral extractable and acid extractable. The extracted pollutants can then be concentrated and analyzed using standard gas chromatography and/or mass spectrometry techniques.

In instances where the water sample is to be analyzed for both base/neutral and acid extractable compounds, the following two-stage single pass procedure may be utilized.

After the aqueous sample to be tested has been placed in holding column 20, its pH is adjusted to greater than 1 using any strong base such as sodium hydroxide. A predetermined amount of solvent is then injected as droplets thorugh nozzle 14 which fall through the sample in a single pass. Base/neutral extractable compounds diffuse through the interface between the solvent droplets and aqueous sample into the solvent and are collected at the bottom of column 20. The amount of solvent used is proportional to the amount of sample contained in the column 20.

After the base/neutral compounds in the extract solution have been collected and drawn off through valve 24, they can be analyzed, or alternatively stored and then combined with the acid extractable compounds for a single analysis. The acid extractable compounds are collected by readjusting the pH of the same aqueous sample to a value less than 2 using a strong mineral acid such as sulfuric acid. A predetermined amount of solvent is then injected as droplets through nozzle 14 in a single pass. Acid extractable compounds diffuse into the solvent through the solvent aqueous interface as the drops fall through the sample. Agitation of the sample during the extraction procedure may enhance the recovery of pollutants by aiding the desired intimate contact between the solvent and aqueous sample. Such agitation could be provided by positioning a mechanical stirrer within the column.

To concentrate the extracted solutions for subsequent analysis, they may be gently heated in a steam bath or the like to cause some solvent to evaporate. A final concentrated extract solution volume would be typically in the range of about 0.1 to 10 ml.

It is understood that the efficiency of the extraction procedure may be observed by the addition of a predetermined amount of one or more surrogate compounds to the aqueous sample prior to the start of the extraction step. The selection of the particular type of surrogate compound will be dependent upon the particular solubility characteristic of the surrogate compounds which may be easily known from the literature. The overall efficiency of the solvent extraction procedure may be easily determined by measuring the concentration of the surrogate compound in the extract solution using the gas chromatograph/mass spectrometry analysis. Various surrogate compounds found useful when methylene chloride is used as a solvent are $D_5$-nitrobenzene, 2-fluorobiphenyl, $D_8$-napthalene 2-fluorophenol, and $D_6$-phenol.

In order that the invention may be better understood, reference is made to the following non-limiting example using known amounts of pollutants and surrogative compounds.

EXAMPLE

To an aliquot of pure water, a number of acid and base/neutral priority pollutant compounds were added as well as the acid and base/neutral surrogate compounds normally used for gas chromatography and mass spectrometry analytical procedures such that the aqueous sample was about 1 liter in volume. The amounts of such compounds and their identification is found in Table 1. The aqueous sample was placed in the holding column 20 of the apparatus of the present invention, and the pH of the sample was adjusted to greater than 11 by the addition of sufficient sodium hydroxide. A first extraction was carried out using 180 ml of methylene chloride solvent which was injected through nozzle into the aqueous sample in the form of substantially uniform droplets. The first extract solution was collected at the bottom of the column and removed.

The pH of the water sample was then adjusted to a value of less than 2 by the addition of sufficient sulfuric acid, and the extraction process was repeated using again 180 ml of solvent. The second extract solution was collected and removed from the column. Then the extract solutions were concentrated to 1.0 ml volumes and the individual resulting concentrates anlayzed using standard gas chromatography and mass spectrometry techniques. Recoveries were reported as follows:

TABLE 1

| B/N COMPOUND | AMOUNT ADDED (μg) | % RECOVERED |
| --- | --- | --- |
| Acenaphthene | 50 | 90 |
| Chrysene | 50 | 72 |
| 1,4 Dichlorobenzene | 50 | 100 |
| Di-n-Butyl Phthalate | 50 | 62 |
| 2,4 Dinitrotoluene | 50 | 74 |
| Di-n-Octyl Phthalate | 50 | 78 |
| N—Nitrosodi-n-Propylamine | 200 | 95 |
| Pyrene | 50 | 84 |
| 1,2,4-Trichlorobenzene | 50 | 98 |
| $D_5$-Nitrobenzene | 100 | 92 |
| 2-Fluorobiphenyl | 100 | 92 |
| $D_8$-Naphthalene | 100 | 95 |
| ACID COMPOUND | | |
| 2-Chlorophenol | 50 | 72 |
| 4-Nitrophenol | 300 | 5 |
| P—Chloro-m-Cresol | 50 | 66 |
| Pentachlorophenol | 50 | 78 |
| Phenol | 50 | 18 |
| 2-Fluorophenol | 100 | 31 |
| $D_6$-Phenol | 100 | 16 |

The above example demonstrates the relative efficiency of the extraction step. For example, the gas chromatography/mass spectrometry analysis of the concentrated extract solution showed that, with respect to Acenaphthene, a 90% extraction recovery was achieved (45 ug) when 50 ug was added to the aqueous sample.

While the methods and apparatus herein described constitute preferred embodiments of the invention, it is to be understood that the invention is not limited to these precise methods and apparatus, and that changes may be made in either without departing from the scope of the invention, which is defined in the appended claims.

What is claimed is:

1. A process for the analysis of organic pollutants contained in an aqueous sample comprising the steps of:
   (a) placing a predetermined amount of an aqueous sample containing one or more extractable organic pollutants in a column to thereby form a volume of sample;
   (b) adjusting the pH of the liquid sample to either an acid, basic, or neutral condition depending upon the organic pollutants to be extracted;
   (c) injecting an extraction solvent under pressure into said sample in a single pass to produce a plurality of substantially uniform droplets, said solvent being substantially immiscible with said sample and having a specific gravity greater than said sample, said pollutants being preferentially soluble in said solvent over said sample, the amount of solvent used being in proportion to the amount of said sample contained in the column,
   (d) contacting said solvent droplets and said sample for a time sufficient for mass transfer of said pollutants from said sample to said solvent to occur by allowing said solvent droplets to settle through the volume of sample in the column and collect at the bottom thereof,
   (e) collecting and removing the resulting extract solution containing one or more of said pollutants,
   (f) analyzing at least a portion of the collected pollutant-containing extract solution.

2. The process of claim 1 in which said aqueous sample is wastewater.

3. The process of claim 1 in which said solvent is selected from the group consisting of methylene chloride, hexane, ethylether and mixtures thereof.

4. The process of claim 1 including the step of agitating the aqueous sample and solvent droplets during contacting of said droplets and aqueous sample.

5. The process of claim 1 including the step of evaporating at least a portion of the extract solution before analysis.

6. The process of claim 1 wherein at least one surrogate compound is added to the aqueous sample prior to injecting solvent into the column.

7. The process of claim 1 wherein the mean diameter of the droplets is between about 0.01 and 0.02 inches.

8. The process of claim 1 wherein the pH is adjusted to a neutral condition.

9. The process of claim 1 wherein the droplets are dispersed throughout the column.

10. The process of claim 9 wherein said droplets are simultaneously projected down the column and outwardly toward its vertical sides.

11. The process of claim 1 in which an inert carrier gas under pressure is used to facilitate injection of said solvent into said aqueous sample.

12. The process of claim 11 in which said inert carrier gas is nitrogen.

13. The process of claim 1 wherein the pH of the liquid sample is adjusted a second time prior to the analyzing step, to a condition different from that resulting from the first adjusting step, and then repeating steps (c), (d), and (e).

14. The process of claim 13 in which the step of adjusting the pH of said aqueous sample the first time is to a pH of greater than 11 before contacting it with said solvent and the second time is to a pH of less than 2.

15. The process of claim 1 in which the pH of the liquid sample is adjusted to a basic condition and further including the steps of readjusting the pH of said aqueous sample to an acid pH after an initial portion of the solvent has been collected and removed, injecting a second portion of the solvent under pressure into said sample in the form of droplets, contacting said second portion of said solvent droplets and sample for a time sufficient for mass transfer of one or more of said pollutants from said sample to said solvent to occur, and collecting and removing a second portion of solvent solution containing one or more of said pollutants.

16. The process of claim 15 including the step of combining the initial and second portions of extract solutions and analyzing for the concentration of pollutants contained therein.

17. A process for the analysis of organic pollutants comprising the steps of:
   (a) placing a predetermined amount of an aqueous sample containing one or more extractable organic pollutants into a column to thereby form a volume of sample;
   (b) adding an amount of a surrogate compound to said aqueous sample;
   (c) adjusting the pH of the aqueous solution to either an acid, basic, or neutral condition depending upon the organic pollutants to be extracted;
   (d) injecting an extraction solvent under pressure downwardly into said sample in a single pass through the column to produce a plurality of substantially uniform droplets which diffuse throughout the column, said solvent being substantially immiscible with said sample and having a specific gravity greater than said sample, said pollutants being preferentially soluble in said solvent over said sample, the amount of solvent used being in proportion to the amount of aqueous sample contained in the column;

(e) contacting said solvent droplets and said sample for a time sufficient for mass transfer of said pollutants from said sample to said solvent to occur by allowing said solvent droplets to settle through the volume of sample in the column and collect at the bottom thereof;

(f) collecting and removing a first resulting extract solution containing one or more of said pollutants;

(g) readjusting the pH of said sample to a condition different than the condition selected in step (c) above;

(h) again injecting an extraction solvent under pressure downwardly into said sample in a single pass through the column to produce a plurality of substantially uniform droplets which diffuse throughout the column, said solvent being substantially immiscible with said sample and having a specific gravity greater than said sample, said pollutants being preferentially soluble in said solvent over said sample, the amount of solvent used being in proportion to the aqueous sample contained in the column;

(i) collecting and removing a second resulting extract solution containing one or more of said pollutants;

(j) combining said first and second extract solutions and analyzing at least a portion of the combined pollutant-containing extract solutions.

* * * * *